US012762701B2

(12) United States Patent
Vöth et al.

(10) Patent No.: US 12,762,701 B2
(45) Date of Patent: Oct. 13, 2026

(54) METHOD AND DEVICE FOR SETTING THE VISIBILITY OF OBJECTS IN A PROJECTION IMAGE GENERATED BY RADIATION

(71) Applicant: Ziehm Imaging GmbH, Nuremberg (DE)

(72) Inventors: Tim Vöth, Nuremberg (DE); Thomas König, Nuremberg (DE); Klaus Hörndler, Nuremberg (DE); Michael Knaup, Reichenschwand (DE); Marc Kachelriess, Nuremberg (DE)

(73) Assignee: Ziehm Imaging GmbH, Nuremberg (DE)

( * ) Notice: Subject to any disclaimer, the term of this patent is extended or adjusted under 35 U.S.C. 154(b) by 238 days.

(21) Appl. No.: 18/757,314

(22) Filed: Jun. 27, 2024

(65) Prior Publication Data

US 2025/0014177 A1 Jan. 9, 2025

(30) Foreign Application Priority Data

Jul. 5, 2023 (EP) .................................... 23183575

(51) Int. Cl.
*G06T 7/00* (2017.01)
*G06T 5/50* (2006.01)
(Continued)

(52) U.S. Cl.
CPC .............. *G06T 7/0012* (2013.01); *G06T 5/50* (2013.01); *G06T 15/00* (2013.01); *G06V 10/764* (2022.01);
(Continued)

(58) Field of Classification Search
CPC ......... G06T 7/0012; G06T 5/50; G06T 15/00; G06T 2207/10116; G06T 2207/20081;
(Continued)

(56) References Cited

U.S. PATENT DOCUMENTS 8,204,292 B2 6/2012 Knapp et al.
9,990,743 B2 6/2018 Knapp et al.
(Continued)

FOREIGN PATENT DOCUMENTS

WO WO 2015/197738 A1 12/2015
WO WO 2019/141544 A1 7/2019

*Primary Examiner* — Jose L Couso
(74) *Attorney, Agent, or Firm* — Knobbe, Martens, Olson & Bear, LLP

(57) ABSTRACT

A method for setting the visibility of objects in a projection image generated by radiation of an anatomical region includes loading imaging data representing a projection image generated by radiation into a memory of a computer, generating a first partial image from the imaging data using a first semantic class by an artificial intelligence device executing an artificial intelligence algorithm, combining the first partial image and the imaging data to generate an output image using a first adjustable function with at least one first parameter such that the first function determines a rendering of the first partial image in the output image, displaying an output image on a display device; and generating training data for training the artificial intelligence algorithm of the artificial intelligence device.

15 Claims, 6 Drawing Sheets

(51) Int. Cl.
*G06T 15/00* (2011.01)
*G06V 10/764* (2022.01)
*G16H 30/40* (2018.01)

(52) U.S. Cl.
CPC .... *G16H 30/40* (2018.01); *G06T 2207/10116* (2013.01); *G06T 2207/20081* (2013.01); *G06T 2207/20221* (2013.01); *G06T 2207/30024* (2013.01)

(58) Field of Classification Search
CPC . G06T 2207/20221; G06T 2207/30024; G06T 12/30; G06T 2207/10081; G06T 2207/20084; G06T 2207/30004; G06T 2211/441; G06T 7/11; G06T 7/194; G06T 7/0014; G06T 7/73; G06T 7/75; G06T 7/174; G06T 5/77; G06T 2207/10121; G06T 2207/30064; G06T 2207/30068; G06T 2207/30048; G06T 2207/30061; G06T 2207/30096; G06T 2210/41; G06T 2207/30101; G06T 2201/031; G06T 3/4046; G06T 5/60; G06T 9/002; G06T 2207/20076; G06V 10/764; G06V 10/25; G06V 10/26; G06V 2201/03; G06V 10/803; G06V 30/274; G06V 10/454; G06V 10/54; G06V 10/7764; G06V 10/774; G06V 10/82; G06V 10/84; G06V 20/41; G06V 30/18057; G06V 20/698; G06V 30/19173; G06V 30/194; G16H 30/40; G16H 20/70; G16H 50/20; G16H 50/30; G16H 30/20; G16H 50/70; A61B 6/5217; A61B 6/5258; A61B 6/4258; A61B 6/5223; G06F 18/251; G06F 18/213; G06F 18/214; G06F 18/22; G06F 18/241; G06F 18/24; G06F 18/2411; G06F 18/2415; G06F 18/253; G06F 30/27; G06N 3/02; G06N 3/08–088; G06N 3/04; G06N 3/0445; G06N 3/0454; G06N 3/0464; G06N 3/4046; G06N 3/4053; G06N 3/049; G06N 3/0499; G06N 7/00; G06N 7/01; G06N 20/00; G06K 7/1482; Y10S 128/925
See application file for complete search history.

(56) References Cited

U.S. PATENT DOCUMENTS

| | | | | |
|---|---|---|---|---|
| 2022/0284542 A1* | 9/2022 | Silver | ........................ | G06T 3/04 |
| 2023/0097849 A1* | 3/2023 | Takahashi | ............. | G06T 7/0012<br>382/131 |

* cited by examiner

METHOD AND DEVICE FOR SETTING THE VISIBILITY OF OBJECTS IN A PROJECTION IMAGE GENERATED BY RADIATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to the field of medical imaging devices and methods, and more specifically to devices and methods for semantic contrast adjustment of X-ray images.

Description of the Related Art

X-ray images are based on the attenuation of X-rays in matter and can have a very high dynamic range, i.e. a large difference between minimum and maximum X-ray and, therefore, image intensities. With non-contrast enhanced, e.g., unaltered imaging on a display device, the relevant areas of the images are often difficult to discern or the local contrast is often too low to differentiate structures. One example is the navigation of instruments, such as guide wires or catheters, in blood vessels that e.g. are located projectively in front of or behind the spinal column and are therefore superimposed by it in the X-ray image.

It is known that, in some cases, the global scaling of image intensities (especially greyscale values) is helpful, for example by adjusting brightness or contrast, or the use of tone value curves or gamma corrections. The disadvantage to these methods is that they influence the entire image by applying a globally valid imaging rule between the input and output values. One way of compressing the image dynamics by increasing the local contrast is to use frequency or bandpass filters in the imaging or Fourier space.

Such filters may also consist of a combination of multiple bandpass filters. However, generally, they primarily remove low frequencies from the Fourier space of the image. As they leave high frequencies largely intact or possibly even increase them, this leads to an attenuation of the image influences of large structures, but also tends to increase image noise relative to the remaining image content. This makes it possible to discern, e.g., a guide wire in front of a spinal column more easily or at all. The result of such methods is that some structures are made more easily discernible to a human observer due to the reduction of the dynamic range, although they actually remove imaging information (in this case preferably low frequencies). Although they have an effect on local contrasting, they also have a global effect, e.g., the same effect everywhere (apart from marginal effects). Such methods are also known from photography, where they are used in high dynamic range (HDR) imaging as tone mapping in order to reduce/compress the high dynamic range of an image to the range that can be displayed by monitors.

WO 2019/141544 A1 relates to a system for image segmentation of an anatomical projection image. The system comprises a data processing system that implements an algorithm for decomposing a projection image generated by irradiating a portion of a subject with imaging radiation. A body region within the irradiated portion is a three-dimensional attenuation structure of an attenuation of the imaging radiation, wherein the attenuation structure is a member of a predefined class of attenuation structures of the segmentation algorithm, thereby representing a classification of the body region. The data processing system segments the projection imaging data using the attenuation structure classification. The segmentation of the projection imaging data essentially separates the contribution of the classified body region to the projection image from the contribution of another body region to the projection image. The further body region overlaps with the classified body region in the projection image.

WO 2015/197738 A1 relates to the visualization of previously suppressed image structures in an X-ray image. A graphical indicator is displayed on the X-ray image to show the suppressed image structure. The devices make showing and hiding the graphical indicator or switching between different graphical representations possible.

U.S. Pat. No. 9,990,743 B2 discloses that image processing techniques may include a methodology for normalizing medical imaging and/or voxel data acquired using different imaging protocols and a methodology for suppressing selected anatomical structures from medical imaging and/or voxel data, which may result in improved imaging and/or improved display of other anatomical structures. For example, the technology disclosed herein can be used to improve the detection of nodules in computed tomography (CT) scans.

U.S. Pat. No. 8,204,292 B2 discloses that a method for extracting one or more components from an image may include normalizing and pre-processing the image to obtain a processed image. Features may be extracted from the processed image. A neural network-based regression can then be performed on the set of extracted features to predict the one or more components. These techniques can be applied, for example, to the extraction and removal of bone components from X-ray images.

SUMMARY

An example problem addressed by certain embodiments of the present technology is that of representing non-anatomical structures during an imaging examination in a positionally correct manner. Without limiting the scope of the present disclosure, certain advantageous features are recited in the claims of the present application.

In a first aspect, a method for setting the visibility of objects in a projection image generated by radiation of an anatomical region includes: loading imaging data representing a projection image generated by radiation into a memory of a computer; generating a first partial image from the imaging data, using a first semantic class by an artificial intelligence device executing an artificial intelligence algorithm, wherein the first semantic class includes at least one of the following semantic classes: a representation of an image of an anatomical structure, a representation of an image of a medical implant, a representation of an image of a medical instrument, and a representation of an image of a medical fastening element; combining the first partial image and the imaging data to generate an output image using a first adjustable function with at least one first parameter, wherein the first adjustable function determines a rendering of the first partial image in the output image, and wherein the at least one first parameter is selected by at least one of the following: at least one user input, a type of anatomical region to be examined, the first semantic class, or the type of medical procedure; displaying an output image on a display device; and generating training data for training the artificial intelligence algorithm of the artificial intelligence device by at least: generating the training data for training the artificial intelligence algorithm of the artificial intelligence device from at least one set of an input image and a first target image; and generating the first target image by replacing, in a region of at least one input image or a region of an image model from which the input image is generated, imaging data representing the first semantic class with imaging data representing the surrounding tissue; wherein each input image corresponds to a projection image of the anatomical region to be examined, which is generated by radiation or the generation of which by radiation is partially or completely simulated; and wherein at least one first target image has imaging information of the first semantic class.

In some embodiments, the rendering of the first partial image in the output image comprises at least a visibility, a brightness, a contrast, or a color of the first partial image in the output image.

In some embodiments, wherein generating the training data for the artificial intelligence algorithm of the artificial intelligence device is performed on an artificial intelligence training device.

In some embodiments, each input image comprises imaging information of the first semantic class.

In some embodiments, the method further includes generating a second partial image from the imaging data, using a second semantic class by an artificial intelligence device executing an artificial intelligence algorithm, wherein the second semantic class includes at least one of the following semantic classes: a representation of an image of an anatomical structure, a representation of an image of a medical implant, a representation of an image of a medical instrument, and a representation of an image of a medical fastening element; and combining the first partial image, the second partial image and the imaging data to generate the output image using a function with the first adjustable function with the at least one first parameter and with a second adjustable function with at least one second parameter, wherein the second function determines the rendering of the second partial image in the output image, and wherein the at least one second parameter is selected by at least one of the following: at least one user input, the type of anatomical region to be examined, the second semantic class, or the type of medical procedure.

In some embodiments, the method further includes: generating an nth partial image from the imaging data, using an nth semantic class by the artificial intelligence device executing an artificial intelligence algorithm, wherein the nth semantic class includes at least one of the following semantic classes: a representation of an image of an anatomical structure, a representation of an image of a medical implant, a representation of an image of a medical instrument, and a representation of an image of a medical fastening element; and combining the partial images 1 to n with the imaging data to generate the output image using a function with n adjustable functions each with at least one parameter, wherein the first to nth function determines the rendering of the first to nth partial image in the output image, and wherein the respective at least one parameter is selected by at least one of the following: at least one user input, the type of anatomical region, the nth semantic class, or the type of medical procedure.

In some embodiments, the input image is generated from a three-dimensional image model of a patient's tissue.

In some embodiments, generating the first target image comprises: selecting a semantic class as a selected class, the imaging information of which is to be retained in the first target image; loading a first three-dimensional image model of a patient's tissue into the memory of the computer, wherein the first three-dimensional image model of the patient's tissue comprises three-dimensional imaging information of the selected semantic class; generating a second three-dimensional image model, which does not comprise imaging information of the selected semantic class by replacing, in a region of the first three-dimensional image model of the patient's tissue, imaging information representing the selected semantic class with imaging information representing the surrounding tissue; generating the input image from the first three-dimensional image model of the patient's tissue; generating at least one intermediate image from the second three-dimensional image model; and generating at least one first target image by subtracting the intermediate image from the input image.

In some embodiments, the three-dimensional image model of the patient's tissue is generated by using three-dimensional X-ray imaging; or the three-dimensional image model of the patient's tissue is generated from a simulation of three-dimensional X-ray imaging.

In some embodiments, the three-dimensional imaging information of the selected semantic class is generated by using three-dimensional X-ray imaging; or the three-dimensional imaging information of the selected semantic class is generated from a simulation of three-dimensional X-ray imaging.

In some embodiments, the method further includes setting the first parameter by a first operating device; setting the second parameter by a second operating device; or setting at least one nth parameter by at least one nth operating device.

In some embodiments, the first parameter, the second parameter, or the nth parameter is a weighting factor.

In some embodiments, the output image is generated as a sum of the projection image generated by radiation; the first parameter multiplied by the first partial image; and the second parameter multiplied by the second partial image.

In some embodiments, the at least one set comprises a second target image comprising imaging information of the second semantic class.

In a second aspect, a medical imaging device comprises: a radiation source configured to emit radiation and a radiation sensor upon which the radiation is incident after passing through an anatomical tissue, wherein the radiation sensor is configured to output radiation data; a projection image generating device configured to generate a projection image from the radiation data; a memory configured to store imaging data representing the projection image generated by radiation; an artificial intelligence device configured to generate a first partial image from the imaging data using a first semantic class by means of an artificial intelligence algorithm, wherein the first semantic class includes at least one of the following semantic classes: a representation of an image of an anatomical structure, a representation of an image of a medical implant, a representation of an image of a medical instrument, and a representation of an image of a medical fastening element; a combination device configured to combine the first partial image and the imaging data to generate an output image using a first adjustable function with at least one first parameter, wherein the at least one first parameter is selected by at least one of the following: at least one user input, a type of anatomical region to be examined, the first semantic class, or a type of medical procedure; a display device configured to display the output image; and an artificial intelligence training device configured for: generating training data for training the artificial intelligence algorithm of the artificial intelligence device based on at least one set of an input image and a first target image; and generating a first target image by replacing, in a region of at least one input image or a region of an image model from which the input image is generated, imaging data representing the first semantic class with imaging data representing the surrounding tissue; wherein each input image corresponds to a projection image of the anatomical region to be examined, which is generated by radiation or the generation of which by radiation is partially or completely simulated; and wherein at least one first target image has imaging information of the first semantic class.

BRIEF DESCRIPTION OF THE DRAWINGS

The invention will now be described in more detail with reference to the figures, which show non-limiting embodiments of the invention, wherein.

DETAILED DESCRIPTION

Figure 1:
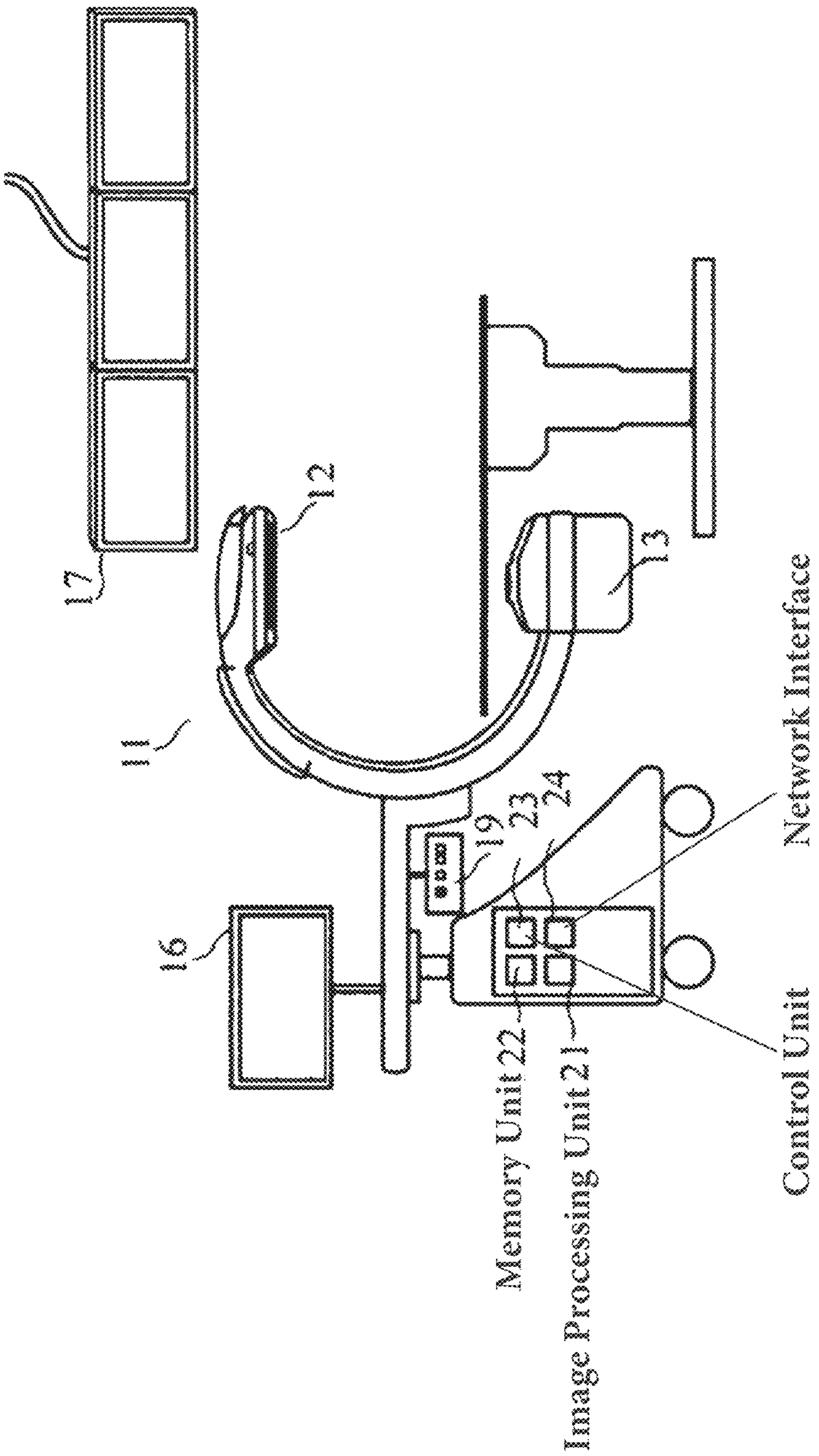
FIG. 1 shows a medical imaging device.

An example problem addressed by the present technology is to provide a method and a device for setting the visibility of objects in a projection image generated by radiation. This example problem can be solved by methods and devices described and claimed in the present disclosure.

The present disclosure includes a method for setting the visibility of objects in a projection image generated by radiation of an anatomical region, wherein imaging data rendering the projection image generated by radiation is loaded into a memory of a computer or a computing unit. A first partial image can be generated from the imaging data using a first semantic class by an artificial intelligence device by means of an artificial intelligence algorithm. The first semantic class can include at least one representation of an image of an anatomical structure, one representation of an image of a medical implant, one representation of an image of a medical instrument or one representation of an image of a medical fastening element. The first partial image and the imaging data can be combined to generate an output image using a first adjustable function with at least one first parameter, wherein the first function determines the rendering of the first partial image in the output image. The at least one first parameter can be selected by at least one user input and/or the type of anatomical region to be examined and/or the first semantic class and/or the type of medical procedure. The output image can be displayed on a suitable display device.

Training data can be generated to train the artificial intelligence algorithm of the artificial intelligence device. The training data for training the artificial intelligence algorithm of the artificial intelligence device can include at least one set of an input image and a first target image. The first target image may be generated by replacing, in a region of at least one input image or a region of an image model from which the input image is generated, imaging data rendering the first semantic class with imaging data rendering the surrounding tissue. Each input image may correspond to a projection image of the anatomical region to be examined, which is generated by radiation or the generation of which by radiation is partially or completely simulated. At least one first target image may have imaging information of the first semantic class.

A plurality of first target images may have the first semantic class, and a second plurality of first target images may not have the first semantic class. The image model may be two-dimensional or three-dimensional. The artificial intelligence device may be a computer which runs software that performs computer generation operations based on artificial intelligence, for example using a neural network. The training data is used to train the artificial intelligence algorithm to perform the step of generating the first partial image via the artificial intelligence device. The projection image can be generated from a three-dimensional image volume.

The rendering of the first partial image in the output image may include at least the visibility and/or the brightness and/or the contrast and/or the color of the first partial image in the output image.

The step of generating the training data for the artificial intelligence algorithm of the artificial intelligence device can be performed on an artificial intelligence training device. The artificial intelligence algorithm may be generated on a training computer or other computer and transferred to the artificial intelligence device. It is understood that the transfer may also comprise storing the artificial intelligence algorithm in a permanent memory. The artificial intelligence algorithm may be trained on the training computer or any other computer using the training data.

Each input image may have imaging information of the first semantic class.

For the viewer of X-ray images, often only structures in the image that belong to certain semantic classes of objects are of interest, while structures that belong to other semantic classes may be disruptive to the viewer. If X-ray imaging is used in minimally invasive vascular surgery, for example, to guide surgical materials such as guide wires, catheters or stents through the patient's body, the surgeon will mainly want to see these surgical materials in the X-ray images. The surgeon will not want to see bones, or not with full contrast, since if they are superimposed on the surgical materials in the X-ray image, the bones can make it difficult to discern the surgical materials. In this case, it would therefore be desirable to enhance the visibility of structures belonging to the "surgical material" semantic class and to reduce the visibility of structures belonging to the "bone" semantic class.

Similarly, when injecting X-ray contrast media, the aim may be to visualize only the semantic class of blood vessels if possible, for which a background image is conventionally subtracted in subtraction methods (e.g., digital subtraction angiography or DSA).

Accordingly, one object of the present technology may be to enhance or reduce the visibility or local contrast of structures in the X-ray image, depending on the semantic class to which these structures belong.

Although many methods which can enhance or reduce the visibility of structures in X-ray images are known, these are not generally based on the semantics of the structures, but on image features which are easier to generate and are used as substitutes, such as the brightness of pixels or the frequency representation (e.g., Fourier transform) of the image.

For example, the use of a tone value curve increases the visibility of structures whose pixel brightness is within a certain brightness range. For example, if increasing the visibility of stents in the image was desired and it was known that they usually appeared dark grey in the image, the visibility of dark grey structures could be increased by applying a suitable tone value curve. However, a disadvantage of a method like this is that the visibility of stents that do not appear dark grey would not be increased and the visibility of dark grey structures that are not stents would be increased. The "dark grey" feature would therefore only be a replacement for the semantic feature "stent", on which the enhanced visibility should be better based.

For each semantic class from a previously defined set of semantic classes, a partial image is generated from an input image, wherein the partial image should only contain the structures of the input image that belong to the respective class. Partial images are generated in such a way that a subtraction makes the appropriate structures invisible.

The partial images and the input image can be recombined so that the visibility of structures belonging to certain semantic classes is reduced or enhanced. The resulting image is referred to below as the output image.

The method may include a second partial image from the imaging data using a second semantic class by the artificial intelligence device using the artificial intelligence algorithm. The second semantic class may include, for example, at least one representation of an image of an anatomical structure, one representation of an image of a medical implant, one representation of an image of a medical instrument, or one representation of an image of a medical fastening element. The method may further combine the first partial image, the second partial image, and the imaging data to generate the output image using a function with a first adjustable function with the at least one first parameter and a second adjustable function with the at least one second parameter. The at least one second parameter can be selected by at least one user input and/or the type of anatomical region to be examined and/or the second semantic class and/or the type of medical procedure. The second function can determine the rendering of the second partial image in the output image.

The rendering of the second partial image in the output image may include at least the visibility and/or the brightness and/or the contrast and/or the color of the second partial image in the output image.

The at least one first parameter can be a measure of how clearly and/or with what level of contrast and/or in what color and/or with what brightness the first semantic class is displayed in the output image or whether it is suppressed. The at least one second parameter can be a measure of how clearly and/or with what level of contrast and/or in what color and/or with what brightness the second semantic class is displayed or suppressed in the output image.

In one example, the anatomical region to be examined may be the chest region of a patient. For example, the operator of a medical imaging device may define a bone as the first semantic class and suppress it as much as possible, and define a stent or guide wire as the second semantic class and enhance its contrast in the output image.

The method can generate an nth partial image from the imaging data using an nth semantic class by the artificial intelligence device using the artificial intelligence algorithm. The nth semantic class may include a representation of an image of an anatomical structure, a representation of an image of a medical implant, a representation of an image of a medical instrument, or a representation of an image of a medical fastening element. The method can combine the partial images 1 to n with the imaging data to generate the output image using a function with n (sub)functions, each with at least one parameter. The respective parameter may be selected by a user input and/or the type of anatomical region to be examined and/or the nth semantic class and/or the type of medical procedure. The first to nth functions determine the rendering of the first to nth partial image in the output image. The rendering of the nth partial image in the output image may include at least the visibility and/or the brightness and/or the contrast and/or the color of the nth partial image in the output image. The respective parameter is a measure of how clearly and/or with what level of contrast and/or in what color and/or with what brightness the nth semantic class is visible in the output image or whether the nth semantic class is suppressed.

The at least one first parameter and/or the at least one second parameter and/or the at least one nth parameter can be selected automatically, for example depending on the anatomical tissue to be examined or the type of medical procedure. In one example, imaging for the healing of a bone fracture may show the bone and screws in higher contrast, whereas soft tissue is displayed in lower contrast. In another example, imaging for the positioning of a stent may suppress bone rendering and show the stent or guide wire in higher contrast. In another example, the type of anatomical tissue to be examined or the type of medical procedure can be determined by the selection of a corresponding organ program by the operator of a medical imaging device.

The input image can be generated from a three-dimensional image model of a patient, for example by means of a projection, in particular a synthetic forward projection.

The step of generating the training data for the artificial intelligence algorithm of the artificial intelligence device may include, for the step of generating the target image by means of at least one set from input image and one or more target images, the step of selecting a semantic class as the selected class, the imaging information of which is to be contained in one of the target images. The method can load a first three-dimensional image model of a patient's tissue into the memory of the computer or computing unit, wherein the first three-dimensional image model of the patient's tissue comprises three-dimensional imaging information of the selected semantic class. The method generates a second three-dimensional image model, which does not comprise imaging information of the selected semantic class, by replacing, in a region of the first three-dimensional image model of the patient's tissue, imaging information representing the selected semantic class with imaging information representing the surrounding tissue. The input image is generated from the first three-dimensional image model of the tissue. An intermediate image is generated from the second three-dimensional image model. The target image is generated by subtracting the intermediate image from the input image.

The input image and the intermediate image can be generated by a forward projection, for example a synthetic forward projection. The three-dimensional image model may be a synthetic image model.

The three-dimensional image model of the patient's tissue may be generated from three-dimensional X-ray imaging, for example computed tomography. In another embodiment, the three-dimensional image model of a patient's tissue may be generated using a simulation of three-dimensional X-ray imaging. In another embodiment, the three-dimensional image model of a patient's tissue may be generated using a statistical model of the patient's tissue.

The three-dimensional imaging information (for example, a three-dimensional image model) of the selected semantic class may be generated using three-dimensional X-ray imaging. In another embodiment, the three-dimensional imaging information of the selected semantic class may be generated by means of a simulation of three-dimensional X-ray imaging.

The first parameter can be set by means of a first operating device and/or the second parameter can be set by means of a second operating device and/or the nth parameter can be set by means of an nth operating device. The first operating device, the second operating device and/or the nth operating device may vary the contrast of the imaging information representing the respective semantic class.

In order for the artificial intelligence device to generate a second partial image from the imaging data, the artificial intelligence algorithm can be trained using corresponding training data. Preferably, this training data can include at least one set including one input image and two target images. The first target image can contain only imaging information from the input image that belongs to the first semantic class. The second target image can contain only imaging information from the input image that belongs to the second semantic class.

The first at least one target image can be generated as described above, e.g., by replacing imaging information in the input image or in an image model from which the input image is generated that belongs to the first semantic class. The second target image can be generated in the same way, e.g., by replacing imaging information in the input image or in an image model from which the input image is generated, which belongs to the second semantic class.

However, the second target image can also be generated in a different way. For example, if the second semantic class were "stent", the synthetic forward projection of a simulated 3D model of a stent could be used as the second target image. Of course, the input image would also have to contain the forward projection of the stent. This could be achieved by using the sum of the second target image and a projection image showing a patient without stents as the input image. It should be noted that although there are two target images in this example, there is only one input image. This means that the input image generated by addition is the same image as the input image in which the imaging information belonging to the first semantic class has been replaced.

The method for expanding from two partial images to n partial images is analogous to the method described above for expanding from one partial image to two partial images.

The first parameter and/or the second parameter and/or the nth parameter can be a weighting factor.

In one example implementation, the output image is generated as follows:

Output image=projection image generated by radiation+first parameter×first partial image+second parameter×second partial image.

The present disclosure also provides a computer program product which, when loaded into a memory of a computer or a computing unit with a processor, performs the steps described above.

The present technology also provides a medical imaging device comprising a radiation source that emits radiation and a radiation sensor upon which the radiation is incident after passing through an anatomical tissue, wherein the radiation sensor outputs radiation data. The radiation sensor may be a flat detector. The medical imaging device can include a projection image generating device that generates a projection image from radiation data. The medical imaging device comprises a memory into which imaging data representing the projection image generated by radiation is loaded. The medical imaging device can further include an artificial intelligence device adapted to generate a first partial image from the imaging data using a first semantic class by means of an artificial intelligence algorithm. The artificial intelligence device can be designed in such a way that it contains a substantially parallel computing architecture, such as a graphics processing unit (GPU), to reduce the computing time. The first semantic class can include at least one representation of an image of an anatomical structure, one representation of an image of a medical implant, one representation of an image of a medical instrument or one representation of an image of a medical fastening element. The artificial intelligence device can further include a combination device configured to combine the first partial image and the imaging data to generate an output image using a first adjustable function with at least one first parameter. The at least one first parameter can be selected by at least one user input and/or the type of anatomical region to be examined and/or the first semantic class and/or the type of medical procedure. The medical imaging device can further include a display device configured to display the output image.

An artificial intelligence training device can be configured to generate training data for training the artificial intelligence algorithm of the artificial intelligence device by means of at least one set of an input image and one or more target images. The artificial intelligence training device can be configured to generate a target image by replacing, in a region of at least one input image or a region of an image model from which the input image is generated, imaging data representing the first semantic class with imaging data representing the surrounding tissue. Each input image can correspond to a projection image of an anatomical region to be examined, which is generated by radiation or the generation of which by radiation is partially or completely simulated. At least one target image can have imaging information of the first semantic class.

The medical imaging device may be further configured as previously described with respect to the method.

The medical imaging device may include a swiveling C-arm. A three-dimensional image model can be created from the radiation data (e.g., by computer tomography).

It is not necessary for the artificial intelligence training device to be part of the medical imaging device. Training data for training the artificial intelligence algorithm can be generated on the artificial intelligence training device, wherein the trained artificial intelligence algorithm is loaded into the artificial intelligence device of the medical imaging device and stored there.

The training data for the artificial intelligence algorithm can be generated on the artificial intelligence training device itself or on another suitable device, wherein in the second case the training data is then fed to the artificial intelligence training device. This may be particularly advantageous if the device for generating the training data and the artificial intelligence device for accelerating the computing efficiency are adapted to their task in different ways.

FIG. 1 shows in a diagram a device according to the present disclosure in the example implementation of a mobile C-arm 11, which is provided for executing the trained artificial intelligence algorithm by means of the artificial intelligence device of the method according to the present disclosure.

The C-arm 11 has an X-ray generator 13 at its first end and an X-ray image detector 12 at its second end and opposite the X-ray generator 13; this may, for example, be a flat detector or an image intensifier. The C-arm 11 is motor-controlled or manually adjustable in several axes in space, wherein the axes may have sensors for detecting the degree of adjustment.

Furthermore, the device includes an image processing unit 21, a memory unit 22, a control unit 23 and a network interface 24. By means of the network interface 24, data, for example imaging data sets and results of the method according to the invention, can be distributed or made available in a network. The image processing unit 21 may include an artificial intelligence device.

The image processing unit 21 includes a memory unit 22, on which the two or three-dimensional imaging data sets used for the method according to the invention can be stored or loaded. These imaging data sets can either be loaded from a server or recorded by means of the C-arm 11 before, during or after a procedure. Furthermore, the memory unit 22 stores instructions which are used for executing the method according to the invention by means of the image processing unit 21. The memory unit 22 can be a non-transitory computer-readable storage medium.

Furthermore, the device may include a graphical user interface with an image output unit 16, 17 and an input unit 19, with which corresponding settings can be set for the image processing unit 21 in corresponding organ programs.

Figure 2:
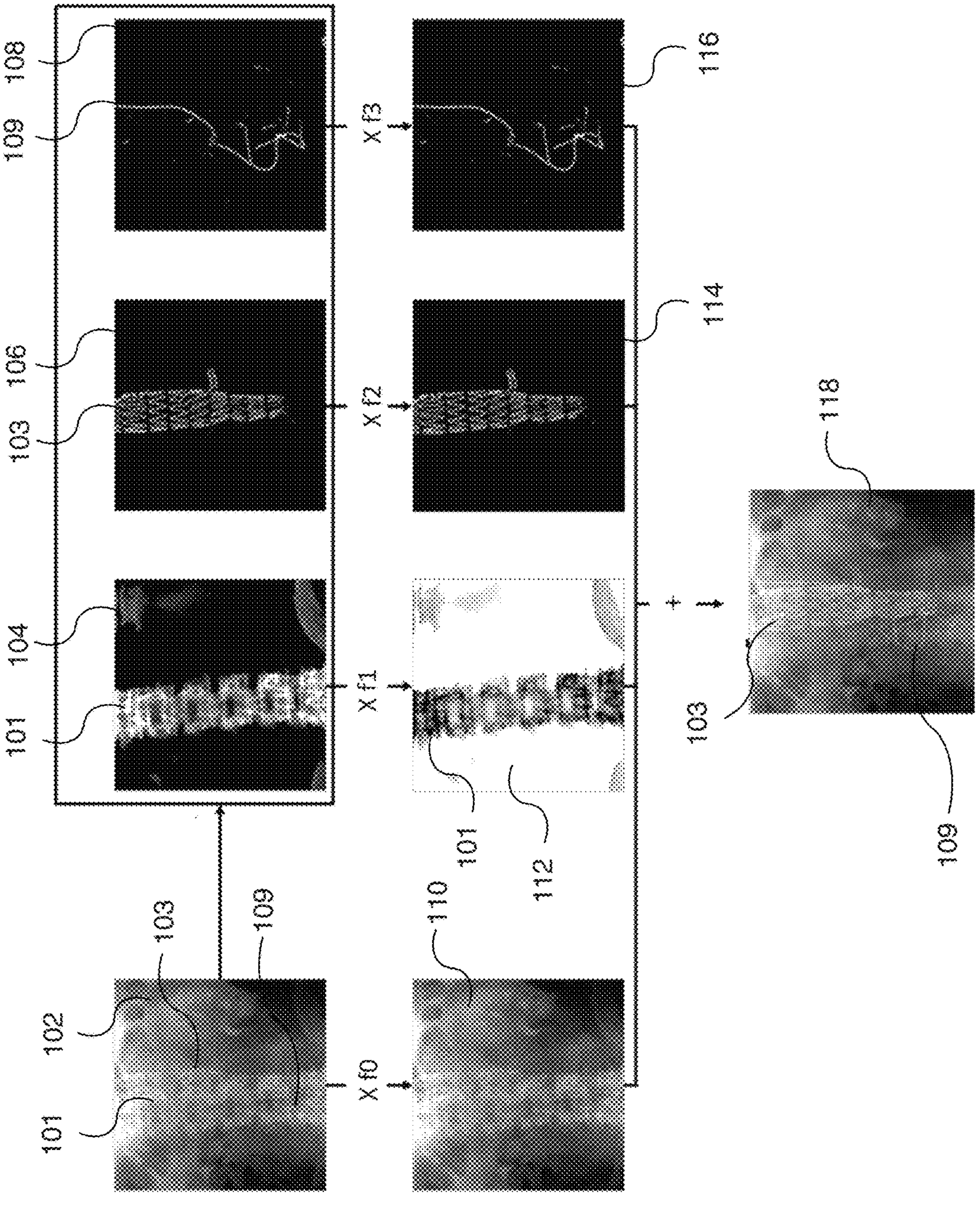
FIG. 2 shows in a diagram the operation of the methods and devices of the present disclosure.

FIG. 2 is a visualization of an example method according to the present disclosure. An input image 102 shows a bone 101, a stent 103 and a guide wire 109. In a first step, partial images 104, 106, 108 are generated from an X-ray image, the input image 102, using the artificial intelligence algorithm running on an artificial intelligence device. Each partial image 104, 106, 108 contains the structures of a particular semantic class. The partial image 104 is the partial image for the "bone" 101 semantic class, the partial image 106 is the partial image for the "stent" 103 semantic class, and the partial image 108 is the partial image for the "guide wire" 109 semantic class.

In a second step, the input image 102 and the partial images 104, 106, 108 are combined. The visibility of structures of certain semantic classes is then reduced in the output image 118, for example the bones 101, or increased, for example the stent 103 and the guide wires 109. In this embodiment, merging is performed by a linear combination. The input image 102 and partial images 104, 106, 108 are multiplied by weighting factors to produce a weighted input image 110 and weighted partial images 112, 114, 116. The weighted input image 110 and the weighted partial images 112, 114, 116 are then added together.

In this example, the formula for combining the input image 102 and the partial images 104, 106, 108 can be described as follows:

$$\text{Output image} = \text{input image} + \text{first weighting factor } f1 \times \text{first partial image} + \text{second weighting factor } f2 \times \text{second partial image} + \text{third weighting factor } f3 \times \text{third partial image.}$$

The weighting factors can be set automatically or by means of a control element.

It is possible to display partial images 104, 106, 108 in color, whereby structures 101, 103, 109 can be highlighted in color.

The methods according to the present disclosure can be used in virtual real time. For example, X-ray images 102 can be processed by the method according to the present disclosure immediately after they have been captured and possibly pre-processed, and the output image 118 is displayed to the viewer. Furthermore, the method can be applied to older input images 102, which are loaded from a patient archive, for example, and to display the output images. The steps also do not have to be performed the same number of times. In particular, it may be advantageous in terms of the computing time required to generate the partial images 104, 106, 108 only once (step 1) and then merge them together several times (step 2), for example to iteratively approximate the desired combination or to separately view combinations that emphasize different aspects of the image.

The input image 102 can be an X-ray image. In some embodiments, a raw X-ray image, e.g., as measured by the detector, is not used; rather, a pre-processed X-ray image may be use. Example pre-processing steps include, e.g., offset correction, gain correction, defect pixel correction, flat field correction or I0 normalization, logarithmization, water pre-correction, scattered beam correction, application of tone value curves, application of high or low-pass filters, application of temporal filters, etc.

The choice of semantic classes can be appropriately orientated towards the current needs of the viewer. For example, the viewer may be able to freely select the semantic classes whose visibility they want to see changed from the set of all semantic classes for which the generation of the corresponding partial images is implemented. It is also conceivable for the semantic classes to be determined by the currently selected organ program, e.g., for the anatomical region to be examined and/or for the type of procedure. In an organ program for vascular procedures, for example, the semantic classes blood vessels, bones, stent, guide wire and catheter would be appropriate. In an organ program for orthopedic procedures, for example, the classes bones, screws and connecting rods would be appropriate.

In order for the input image 102 and the partial images 104, 106, 108 to be merged together in step 2 so that the output image 118 meets the viewer's requirements, the exact pixel values of the partial images 104, 106, 108 may be important. For example, the partial images can be generated in such a way that a simple subtraction of a partial image 104, 106, 108 from the input image 102 produces an output image in which the structures of the semantic class of the partial image 104, 106, 108 are as suppressed as fully as possible. The subtraction is a special case of the merging performed in step 2.

A physically motivated approach would include generating the partial images 104, 106, 108 in such a way that the partial images contain the physical contribution of the structures of the respective semantic class to the input image. However, such partial images may not be suitable for the above-mentioned subtraction, because after subtraction of a partial image, the structures of the corresponding semantic class would remain visible as a "negative imprint", i.e. with inverted contrast, in the output image 118.

Figure 3:
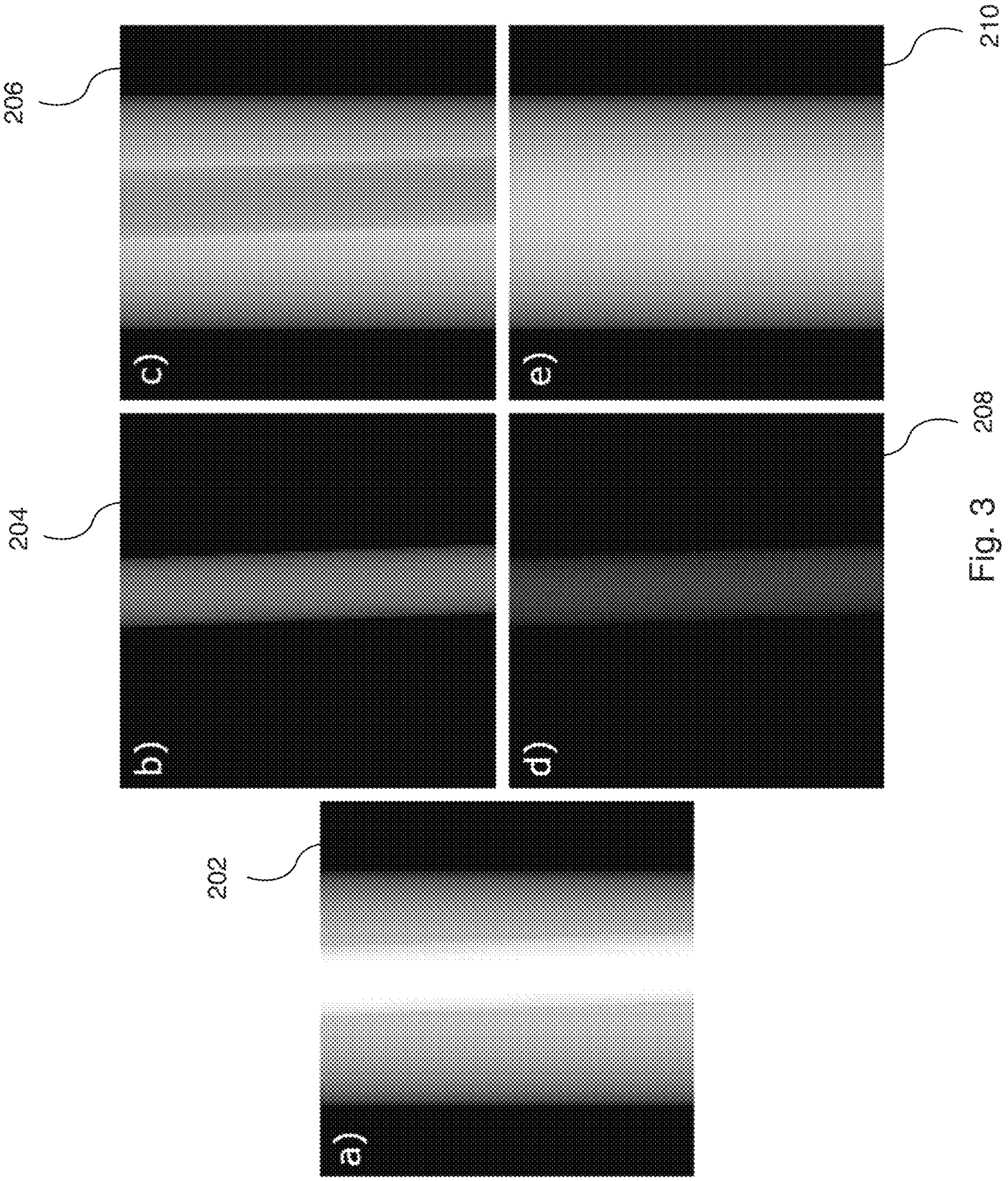
FIG. 3 shows a diagrammatic representation of example input images, partial images and output images in the application of an already trained artificial intelligence algorithm.

This effect is shown in a diagram in FIG. 3 using the example of a partial bone image. If the physical partial bone image 204 is subtracted from the input image 202, the first output image 206 will still show the bones in an undesirable manner, however with inverted contrast. This effect is easy to understand if it is considered that the input image is only composed of the contributions of soft tissue and bone. If the bone contribution is now removed by subtracting the physical partial bone image, only the soft tissue contribution remains in the output image, leaving a correspondingly empty area at the site of the bone.

However, as there are then bone-shaped cavities in the patient's soft tissue, these bone-shaped cavities are visible in the output image, particularly because there can be no soft tissue where there is bone.

In order to avoid this effect, each of the partial images can be generated such that, after subtracting a partial image from the input image, the structures of the respective semantic class are actually invisible in the output image. This distinguishes the present methods from the physically motivated approaches of the prior art described above. A partial bone image 208 generated in this way can be seen in FIG. 3. After subtracting this partial bone image from the input image 202, the bones are invisible in the second output image 210.

FIG. 3 shows a diagrammatic representation of exemplary input images, partial images and output images in the application of an already trained artificial intelligence algorithm. In this example, "bone" is the only semantic class. The input image 202 is a simplified model of an X-ray image of a thigh, wherein the bone is shown as a white area inside. The partial bone image 204 was generated in accordance with the physical approach, according to which the partial bone image 204 is equal to the physical contribution of the bones to the input image. In the first output image 206, which is obtained by subtracting the partial bone image 204 from the input image 202, the bones are still visible but with inverted contrast; while the bones in the input image 202 are brighter than the surroundings, they are darker in the first output image 206.

In contrast, the partial bone image 208, generated according to the present disclosure, has been generated in such a way that after subtraction of the partial bone image 208 from the input image 202, the bones are invisible. In the second output image 210, which is obtained by subtracting the partial bone image 208 according to the present disclosure from the input image 202, the bones are invisible. This is more in line with the expectations of human observers than in the first output image 206.

Ideally, the partial images 104, 106, 108 can be generated by a machine learning process (MLP), for example an artificial neural network (NN), preferably a convolutional neural network (CNN), whose input is the input image and whose outputs are the partial images. Although "MLP" is used in the singular form in the following, it may be advantageous to use multiple MLPs, each displaying only one partial image 104, 106, 108 or multiple partial images 104, 106, 108. For example, the generation of the partial images could be more accurate or efficient if a separate MLP were used for each semantic class.

Before an MLP can carry out tasks, it has to be trained. One of the ways in which this can be done is by using supervised training. In supervised training, an MLP learns from a large number of input element-output element sets (input-output sets). Each set comprises an input element and an output element. In the context of the present invention, the input element of such a set would be an input image. The output element of the set would be a target image associated with the input image or several target images associated with the input image. A target image associated with the input image is understood to be a partial image associated with the input image that is as ideal as possible, i.e. a partial image that the MLP would ideally display if it received the input image as input. As MLPs do not usually work perfectly, partial images (which are what the MLP actually displays) and target images (what the MLP should display) do differ.

It would be reasonable to initially expect to be able to obtain the number of input element-output element sets required for successful training from real clinical data in the form of X-ray projections (2D). However, on the one hand these are difficult to obtain (data protection guidelines, patient consent, contracts with clinics, etc.), and on the other hand, target images also cannot be obtained from them, as the contributions of the semantic classes associated with the target images are superimposed by the contributions of other structures in the X-ray images. In other words, creating an output element here with justifiable expenditure would not be possible, which means that the training of the MLP cannot be carried out.

The inventors of the present technology have recognized that the idea of generating the input element-output element sets at least in part by realistic simulation shows more promise. For example, a simulation of an input element-output element set could be based on a 3D model of a patient that contains no objects of the semantic classes and 3D models of objects of the semantic classes. A 3D model in this context means any three-dimensional representation of an object, including real patient data. For example, voxel volumes (i.e. also computer tomographies), triangular grids and CAD models are 3D models. By combining all 3D models (patient and objects of the semantic classes) an overall model would be obtained. A simulated X-ray image generated by synthetic forward projection (digitally reconstructed radiograph (DRR)) of the overall model can then be used as the input image.

An associated target image can be generated by subtracting a fictitious input image from the input image, wherein the fictitious input image is generated by synthetic forward projection of a fictitious overall model. The fictitious overall model is generated by replacing the objects of the semantic class (corresponding to the target image to be generated) in the overall model with the surrounding materials.

Figure 4:
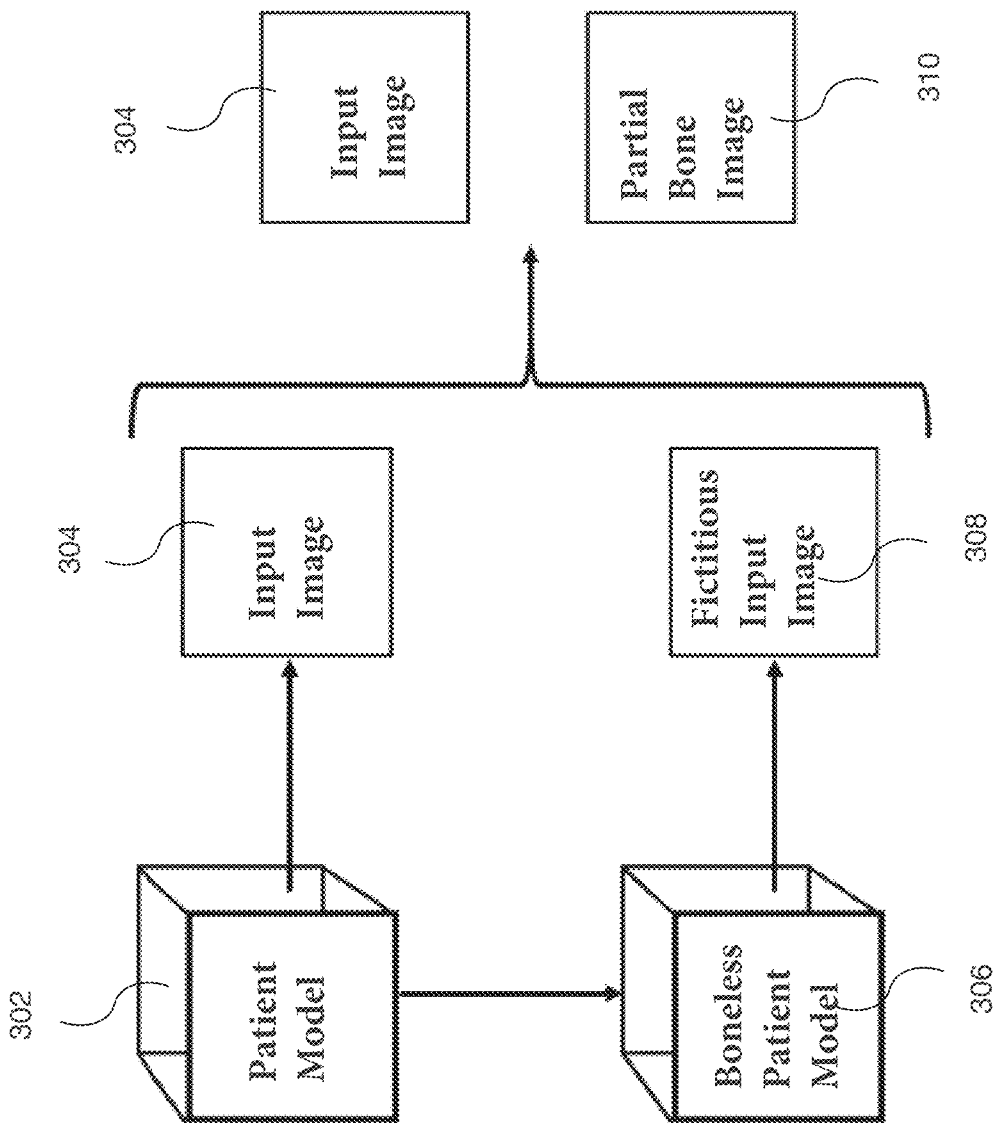
FIG. 4 shows in a diagram the training of an artificial intelligence device if a semantic class is to be trained.
Figure 5:
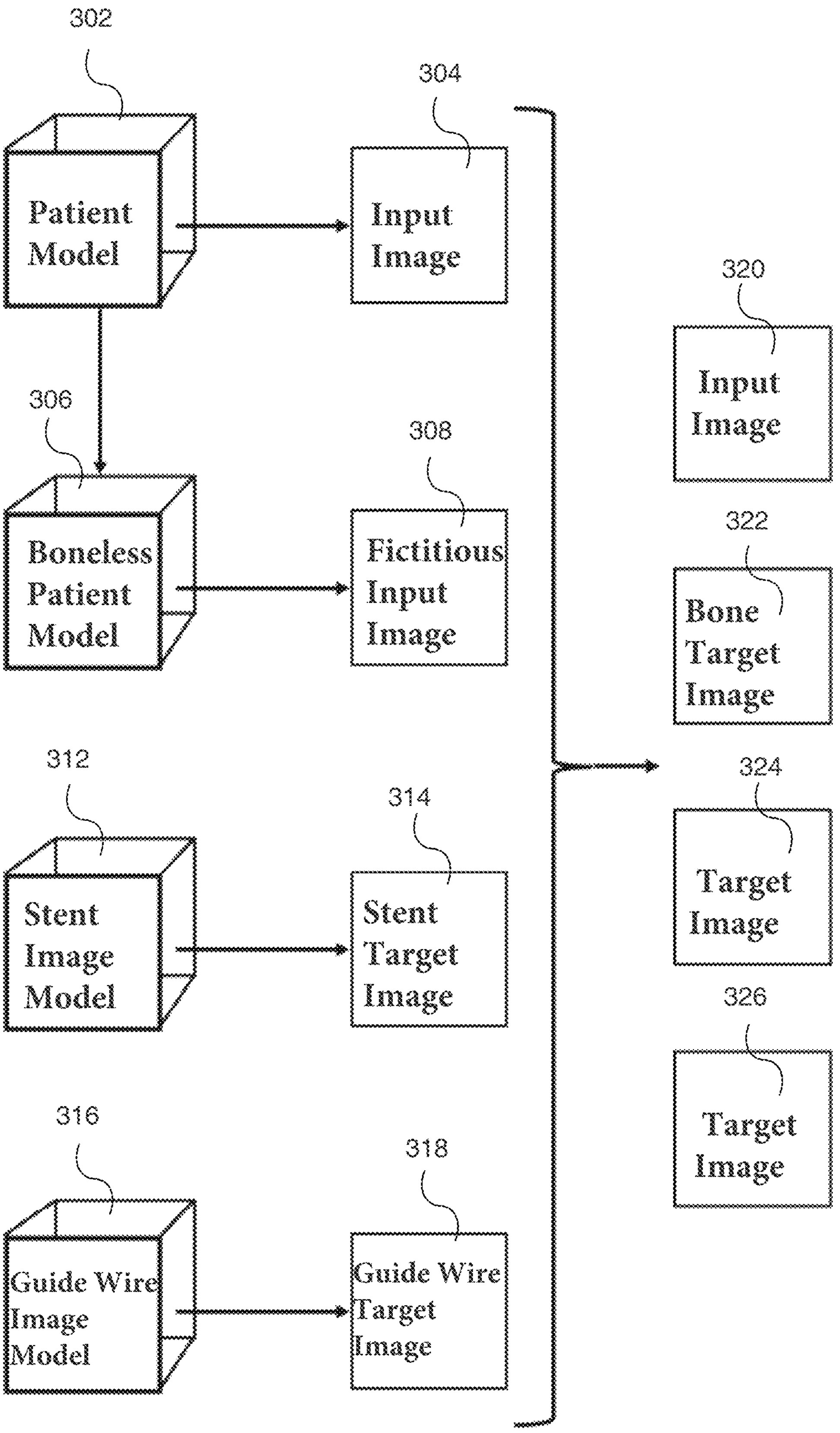
FIG. 5 shows in a diagram the training of an artificial intelligence device if several semantic classes are to be trained.

The method for simulating input element-output element sets is shown in a diagram in FIGS. 4 and 5. The simulation of input images and target images described in this paragraph is only necessary for training the MLP, but not during its application. It ensures that after subtraction of a partial image or target image from the input image, no negative imprint of the structures of the semantic class is created (as in the first output image 206, but the structures of the semantic class are actually invisible as in the second output image 210).

The 3D models on which the simulation of the training data described above is based can, for example, be obtained by simulation or from CT volumes. For example, a 3D model of a patient can be generated from a clinical CT volume of a patient. Segmentation can also be used to generate 3D models of bones or vessels containing contrast medium from a CT volume. Furthermore, 3D models of objects of semantic classes can be generated by suitable simulation. For example, a guide wire can be modelled as a curved cylinder the center line of which is given by a polynomial train with randomly selected control points. By combining a large number of 3D models and generating a large number of DRRs per overall model, a large training data set can be generated. Once the MLP has been trained with this training data set, it can be applied to any X-ray images. 3D models are then no longer necessary.

FIG. 4 shows an example of the generation of training data if the artificial intelligence is to be trained on just one semantic class. In this example, the semantic class is "bones".

The input image 304 is a forward projection, for example a synthetic forward projection, of a patient model 302. The input image thus contains soft tissue and bone in particular.

To generate the bone target image 310, all bones in the patient model 302 are first replaced by soft tissue in order to generate a boneless patient model 306. A forward projection 308, for example a synthetic forward projection, is then generated from this boneless patient model 306, which generates a first fictitious input image 308. The forward projection 308 thus corresponds to the first fictitious input image, i.e. the input image in which the bones have been replaced by soft tissue. The partial bone image 310 is then the difference between the input image 304 and the fictitious input image 308.

The input image 304 and the partial bone image 310 are used to train the artificial intelligence. Artificial intelligence training is known by the person skilled in the art.

In particular, publicly available software libraries exist for this purpose, such as Tensorflow or PyTorch, which provide various modem artificial intelligence algorithms and corresponding architectures, for example convolutional neural networks, such as U-nets. These can then be integrated into programming languages such as C++ or Python in a comparatively simple manner. Furthermore, these libraries provide extensive auxiliary material to make training the artificial intelligence algorithms or the artificial intelligence device as simple as possible, e.g. by replicating and adapting training data by rotation, reflection, contrast changes, etc.

The artificial intelligence algorithm can be trained e.g. using supervised training. In supervised training, the artificial intelligence algorithm is presented with at least one input-output set. In our case, the input part of such a set consists of the input image. In our case, the output part of such a set consists of the target images.

FIG. 5 shows an example of the generation of training data when the artificial intelligence is to be trained on several semantic classes. In this example, the semantic classes are "bone", "stent" and "guide wire".

The input image 320 is generated by adding a forward projection of a stent model (stent target image 314) and a forward projection of a guide wire model (guide wire target image 318) to the forward projection of the patient model 304. Thus, the input image 320 contains, in particular, soft tissue, bone, at least one stent and at least one guide wire.

To generate the boneless patient model 306, all bones in the patient model are first replaced by soft tissue, as described with reference to FIG. 4. The bone target image 322 is generated by subtracting a forward projection 308 of the boneless patient model 306 from a forward projection 304 of the patient model 302, as described with reference to FIG. 4.

The stent target image 314 is generated by a forward projection from a three-dimensional stent image model 312 comprising one or more stents. The guide wire target image 318 is generated by a forward projection from a three-dimensional guide wire image model 316 comprising one or more guide wires.

The input image 320 and the target images 322, 324, 326 are later used to train the artificial intelligence device and/or the artificial intelligence algorithm. Of the several target images 322, 324, 326 (three target images are used in this embodiment), at least one target image 322 (in this embodiment, the bone target image 322) is generated by the replacement-subtraction method. The other target images 324, 326 may be generated differently (in this example by forward projection of corresponding 3D models).

Figure 6:
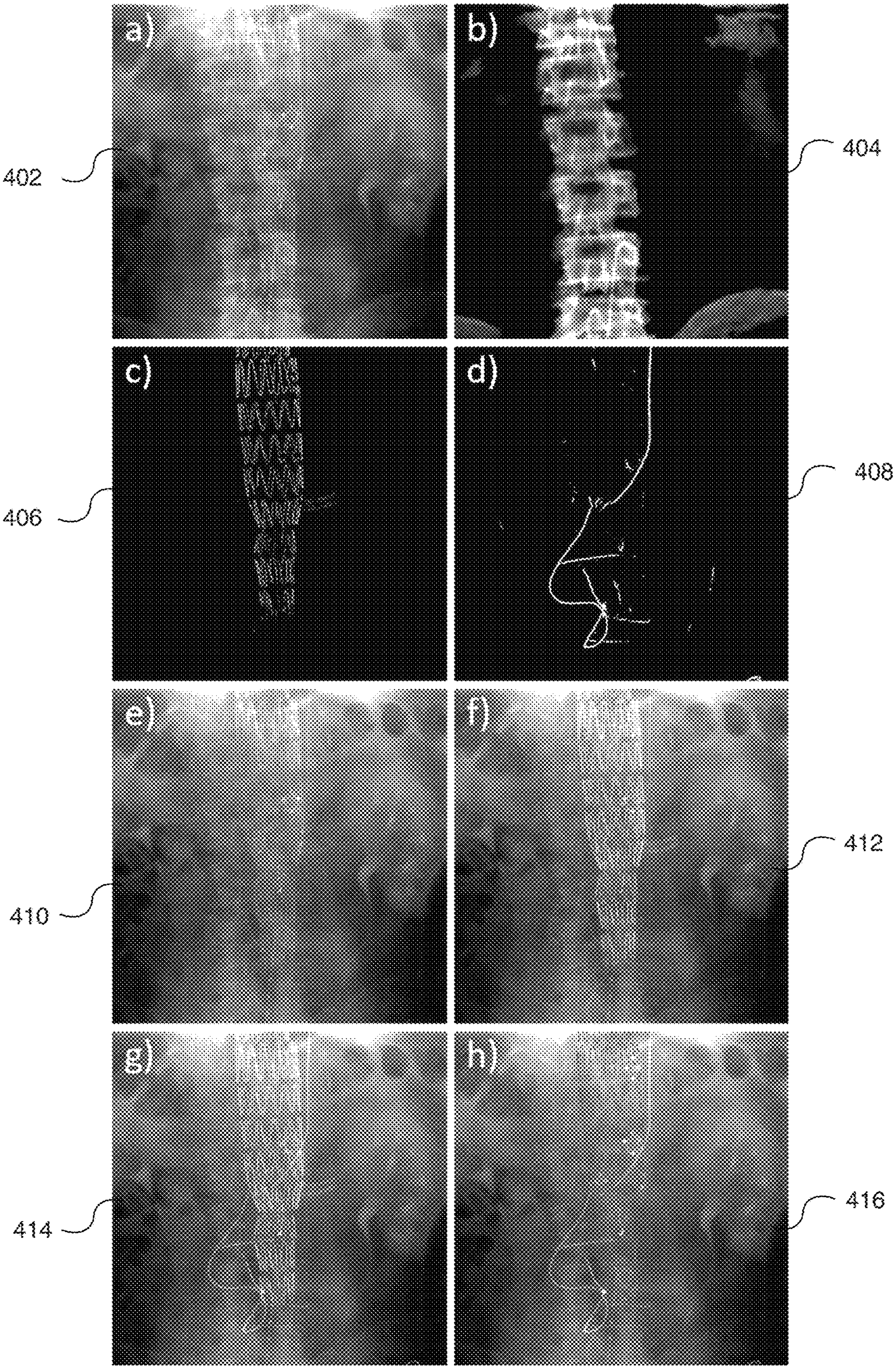
FIG. 6 shows various options for merging the input image and partial images.

FIG. 6 shows an input image 402, a partial bone image 404, a partial stent image 406, and a partial guide wire image 408. In the first output image 410, the visibility of the bones has been reduced. In the second output image 412, the visibility of a stent has also been enhanced. In the third output image 414, the visibility of guide wires has also been enhanced. In the fourth output image 416, the stent has also been highlighted by coloring the partial stent image 406 before merging.

The input image 402 and the partial images 404, 406 and 408 are merged with the aim of enhancing or decreasing the visibility of structures of certain semantic classes in the resulting output image 410, 412, 414, 416 in relation to the visibility in the input image. Whether and to what extent the visibility of structures of a given semantic class is enhanced or reduced is ideally based on the viewer's requirements at the time. This could be defined in an organ program, for example. For example, in vascular procedures, it is likely that the visibility of bones will need to be reduced and the visibility of surgical material (e.g. stents, guide wires, etc.) enhanced, or that only blood vessels containing contrast medium and surgical material will need to be shown.

FIG. 6 shows various options for merging the input image 402, the partial bone image 404, the partial stent image 406 and the partial guide wire image 408. Another way of determining whether and to what level the visibility of a semantic class should be changed is to provide the viewer with a control element, for example on a touch-sensitive screen. The direction and extent of actuation of the control element would then control whether and to what extent the visibility is reduced or increased (semantic contrast controller according to the invention).

Furthermore, it may be advantageous to determine the combination process automatically and in real time, for example because it is preferable for the user not to have to set the combination process and the combination process that may have been set in the organ program may not be appropriate for every situation. This automatic setting can be done, for example, by optimizing a target function, such as by a gradient-based optimization method, a Nelder-Mead optimization method or methods from the field of non-convex or global optimization. For example, such a target function could be based on the histograms of the images and/or measure the typical contrast between the structures of different semantic classes and/or structures of the input image. The target function may also be generated only on certain regions of the images, wherein the regions are generated from one or more of the partial images (for example, by thresholding and morphological operations). Because optimization may be too slow for some real-time applications, it may be advantageous to use other, faster algorithms to determine the combination factors. For example, an MLP that has been trained to estimate the optimum combination settings could be used.

In practice, merging may be performed, for example, by linear combination of the input image 102 and partial images 104, 106, 108, as shown in FIG. 2. By linear combination, the inventors mean that each of the aforementioned images is multiplied by a generally real-valued factor (positive, zero or negative) and the images are then added together.

Before merging, the images may be colored or their color may be changed. For example, stents could be shown in red while the rest of the image content is shown in grey scale (see 416 in FIG. 6). Different color channels may be dealt with in different ways during the merging process. Prior to merging, the input image and/or the partial images may also be processed in other ways. For example, because the generation of the partial images does not work perfectly, parts of a guide wire could be included in the partial bone image (false-positive results, see above). If the visibility of bones were then reduced, the visibility of the guide wire would be reduced at the same time. To prevent this, it could be advantageous, for example, to remove any visible guide wires from the partial bone image, for example by applying a low-pass filter to the bone image.

According to the present disclosure, whether and to what level the visibility of a semantic class is to be changed is set. One option is to provide the viewer with a control element, for example on a touch-sensitive screen. The direction and extent of actuation of the control element would then control whether and to what extent the visibility is reduced or increased (semantic contrast controller according to the invention). Another option is to define the visibility of a semantic class depending on the medical procedure.

What is claimed is:

1. A method for setting the visibility of objects in a projection image generated by radiation of an anatomical region, the method comprising:

loading imaging data representing a projection image generated by radiation into a memory of a computer;

generating a first partial image from the imaging data, using a first semantic class by an artificial intelligence device executing an artificial intelligence algorithm, wherein the first semantic class includes at least one of the following semantic classes: a representation of an image of an anatomical structure, a representation of an image of a medical implant, a representation of an image of a medical instrument, and a representation of an image of a medical fastening element;

combining the first partial image and the imaging data to generate an output image using a first adjustable function with at least one first parameter, wherein the first adjustable function determines a rendering of the first partial image in the output image, and wherein the at least one first parameter is selected by at least one of the following: at least one user input, a type of anatomical region to be examined, the first semantic class, or the type of medical procedure;

displaying an output image on a display device; and generating training data for training the artificial intelligence algorithm of the artificial intelligence device by at least:

generating the training data for training the artificial intelligence algorithm of the artificial intelligence device from at least one set of an input image and a first target image; and generating the first target image by:

replacing, in a region of a first three-dimensional image model of the patient's tissue from which the input image is generated, imaging data representing the first semantic class with imaging data representing the surrounding tissue, to generate a second three-dimensional image model; and generating at least one first target image based at least in part on an image generated from the second three-dimensional image model;

wherein each input image corresponds to a projection image of the anatomical region to be examined, which is generated by radiation or the generation of which by radiation is partially or completely simulated; and wherein at least one first target image has imaging information of the first semantic class.

2. The method of claim 1, wherein the rendering of the first partial image in the output image comprises at least a visibility, a brightness, a contrast, or a color of the first partial image in the output image.

3. The method of claim 1, wherein generating the training data for the artificial intelligence algorithm of the artificial intelligence device is performed on an artificial intelligence training device.

4. The method of claim 1, wherein each input image comprises imaging information of the first semantic class.

5. The method of claim 1, further comprising:

generating a second partial image from the imaging data, using a second semantic class by an artificial intelligence device executing an artificial intelligence algorithm, wherein the second semantic class includes at least one of the following semantic classes: a representation of an image of an anatomical structure, a representation of an image of a medical implant, a representation of an image of a medical instrument, and a representation of an image of a medical fastening element; and combining the first partial image, the second partial image and the imaging data to generate the output image using a function with the first adjustable function with the at least one first parameter and with a second adjustable function with at least one second parameter, wherein the second function determines the rendering of the second partial image in the output image, and wherein the at least one second parameter is selected by at least one of the following: at least one user input, the type of anatomical region to be examined, the second semantic class, or the type of medical procedure.

6. The method of claim 5, further comprising:

generating an nth partial image from the imaging data, using an nth semantic class by the artificial intelligence device executing an artificial intelligence algorithm, wherein the nth semantic class includes at least one of the following semantic classes: a representation of an image of an anatomical structure, a representation of an image of a medical implant, a representation of an image of a medical instrument, and a representation of an image of a medical fastening element; and combining the partial images 1 to n with the imaging data to generate the output image using a function with n adjustable functions each with at least one parameter, wherein the first to nth function determines the rendering of the first to nth partial image in the output image, and wherein the respective at least one parameter is selected by at least one of the following: at least one user input, the type of anatomical region, the nth semantic class, or the type of medical procedure.

7. The method of claim 1, wherein the input image is generated from a three-dimensional image model of a patient's tissue.

8. The method of claim 1, wherein generating the first target image comprises:

selecting a semantic class as a selected class, the imaging information of which is to be retained in the first target image;

loading the first three-dimensional image model of a patient's tissue into the memory of the computer, wherein the first three-dimensional image model of the patient's tissue comprises three-dimensional imaging information of the selected semantic class;

generating the second three-dimensional image model, which does not comprise imaging information of the selected semantic class by replacing, in a region of the first three-dimensional image model of the patient's tissue, imaging information representing the selected semantic class with imaging information representing the surrounding tissue;

generating the input image from the first three-dimensional image model of the patient's tissue;

generating at least one intermediate image from the second three-dimensional image model; and generating the at least one first target image by subtracting the intermediate image from the input image.

9. The method of claim 8, wherein:

the three-dimensional image model of the patient's tissue is generated by using three-dimensional X-ray imaging; or the three-dimensional image model of the patient's tissue is generated from a simulation of three-dimensional X-ray imaging.

10. The method of claim 8, wherein:

the three-dimensional imaging information of the selected semantic class is generated by using three-dimensional X-ray imaging; or the three-dimensional imaging information of the selected semantic class is generated from a simulation of three-dimensional X-ray imaging.

11. The method of claim 1, further comprising:

setting the first parameter by a first operating device;

setting the second parameter by a second operating device; or setting at least one nth parameter by at least one nth operating device.

12. The method of claim 1, wherein the first parameter is a weighting factor.

13. The method of claim 5, wherein the output image is generated as a sum of:

the projection image generated by radiation;

the first parameter multiplied by the first partial image; and the second parameter multiplied by the second partial image.

14. The method of claim 5, wherein the at least one set comprises a second target image comprising imaging information of the second semantic class.

15. A medical imaging device comprising:

a radiation source configured to emit radiation and a radiation sensor upon which the radiation is incident after passing through an anatomical tissue, wherein the radiation sensor is configured to output radiation data;

a projection image generating device configured to generate a projection image from the radiation data;

a memory configured to store imaging data representing the projection image generated by radiation;

an artificial intelligence device configured to generate a first partial image from the imaging data using a first semantic class by means of an artificial intelligence algorithm, wherein the first semantic class includes at least one of the following semantic classes: a representation of an image of an anatomical structure, a representation of an image of a medical implant, a representation of an image of a medical instrument, and a representation of an image of a medical fastening element;

a combination device configured to combine the first partial image and the imaging data to generate an output image using a first adjustable function with at least one first parameter, wherein the at least one first parameter is selected by at least one of the following: at least one user input, a type of anatomical region to be examined, the first semantic class, or a type of medical procedure;

a display device configured to display the output image; and an artificial intelligence training device configured for:

generating training data for training the artificial intelligence algorithm of the artificial intelligence device based on at least one set of an input image and a first target image; and generating the first target image by:

replacing, in a region of a first three-dimensional image model of the patient's tissue from which the input image is generated, imaging data representing the first semantic class with imaging data representing the surrounding tissue, to generate a second three-dimensional image model; and generating at least one first target image based at least in part on an image generated from the second three-dimensional model;

wherein each input image corresponds to a projection image of the anatomical region to be examined, which is generated by radiation or the generation of which by radiation is partially or completely simulated; and wherein at least one first target image has imaging information of the first semantic class.

* * * * *